US007153135B1

(12) United States Patent
Thomas

(10) Patent No.: US 7,153,135 B1
(45) Date of Patent: Dec. 26, 2006

(54) METHOD FOR AUTOMATICALLY CREATING A DENTURE USING LASER ALTIMETRY TO CREATE A DIGITAL 3-D ORAL CAVITY MODEL AND USING A DIGITAL INTERNET CONNECTION TO A RAPID STEREOLITHOGRAPHIC MODELING MACHINE

(76) Inventor: Richard J. Thomas, 7097 Bonaire Ct., Rockford, MI (US) 49341

( * ) Notice: Subject to any disclaimer, the term of this patent is extended or adjusted under 35 U.S.C. 154(b) by 1138 days.

(21) Appl. No.: 09/712,081

(22) Filed: Nov. 14, 2000

Related U.S. Application Data

(60) Provisional application No. 60/165,474, filed on Nov. 15, 1999.

(51) Int. Cl.
*A61C 3/00* (2006.01)
(52) U.S. Cl. ........................ 433/213; 433/214; 433/223
(58) Field of Classification Search .................. 433/71, 433/213, 214, 223
See application file for complete search history.

(56) References Cited

U.S. PATENT DOCUMENTS

| | | | |
|---|---|---|---|
| 4,324,546 A | 4/1982 | Heitlinger et al. | 433/433 |
| 4,575,805 A | 3/1986 | Moermann et al. | 364/364 |
| 4,611,288 A | 9/1986 | Duret et al. | 364/354 |
| 4,833,617 A | 5/1989 | Wang | 364/364 |
| 4,837,732 A | 6/1989 | Brandestiini et al. | 364/356 |
| 4,935,635 A | 6/1990 | O'Harra | 205/250 |
| 4,964,770 A | 10/1990 | Steinbichler et al. | 433/433 |
| 5,027,281 A | 6/1991 | Rekow et al. | 364/364 |

(Continued)

OTHER PUBLICATIONS

Liedtke New 3-D Computer System Takes the Metal Out of Straightening Teeth The Grand Rapids Press Sep. 24, 2000 A9.

(Continued)

*Primary Examiner*—Nicholas D. Lucchesi
(74) *Attorney, Agent, or Firm*—William L. Muckelroy; Arthur L. Lessler; Gary Lipson

(57) ABSTRACT

A method is presented for rapidly making and delivering directly to a consumer a full upper and/or lower denture on the basis of contemporaneous digital image information laser scanned from the person's oral cavity after all respective upper and/or lower teeth have been removed, the delivery of the denture occurring substantially contemporaneously with the creation of the contemporaneous digital image information and optionally including and based on archived digital image information laser scanned from the person's oral cavity before all respective upper and/or lower teeth have been removed and digitally stored. According to which this contemporaneous digital image information and archival digital image information of the oral cavity is converted, by means of what is called the rapid prototyping technique and thus with a processing step (20) and a combination of an optional laser scanning step (18) solely for archiving the oral cavity when upper and/or lower teeth are present and a repetition of the laser scanning step (18) at a subsequent time when upper and/or lower teeth have been removed, a pre-selected block of plastic is used in a processing step (26) at a remote rapid modeling facility for receiving and processing digital information to form the block of plastic or like material into a denture of which at least a part is formed to substantially perfectly fit in juxtaposed relationship to the corresponding gums of the consumer. At least, pre-selected outer or non-juxtaposing is selected for manufacture of the denture using an arbitrary archived digital image not derived from the consumer's oral cavity image but selected by the consumer for its style, cosmetic characteristics, for example, color of teeth, size and variety of teeth, and/or perceived suitability.

7 Claims, 2 Drawing Sheets

U.S. PATENT DOCUMENTS

| | | | | |
|---|---|---|---|---|
| 5,092,022 | A | 3/1992 | Duret | 39/433 |
| 5,189,781 | A | 3/1993 | Weiss et al. | 29/164 |
| 5,224,049 | A | 6/1993 | Mushabac | 364/264 |
| 5,257,184 | A | 10/1993 | Mushabac | 354/433 |
| 5,413,481 | A | 5/1995 | Goppel et al. | 433/356 |
| 5,448,472 | A | 9/1995 | Mushabac | 364/364 |
| 5,452,219 | A | 9/1995 | Dehoff et al. | 364/364 |
| 5,527,182 | A | 6/1996 | Willoughby | 433/433 |
| 5,557,397 | A | 9/1996 | Hyde et al. | 356/356 |
| 5,605,459 | A | 2/1997 | Kuroda | 433/433 |
| 5,676,850 | A | 10/1997 | Reed et al. | 216/216 |
| 5,718,585 | A | 2/1998 | Dehoff et al. | 433/433 |
| 5,725,376 | A | 3/1998 | Poirer | 433/433 |
| 5,768,134 | A | 6/1998 | Swaelens et al. | 364/623 |
| 5,823,778 | A | 10/1998 | Schmitt et al. | 433/433 |
| 5,908,299 | A | 6/1999 | Dehoff et al. | 433/433 |
| 5,940,170 | A | 8/1999 | Berg et al. | 365/365 |
| 6,261,098 | B1 * | 7/2001 | Persson | 433/213 |
| 6,364,661 | B1 * | 4/2002 | Brattesani | 433/37 |
| 6,767,208 | B1 * | 7/2004 | Kaza | 433/24 |

OTHER PUBLICATIONS

Scope of Services from orthodontics.net Oct. 12, 2000 (date of download; date of publication unknown).

Graham New Topgraphic Map May Explain Martian History Astronomy Sep. 1999 p. 24.

A New Look at the Martian Landscape Science vol. 284, May 28, 1999 p. 1441.

Physical Item: Mars Global Surveyor (MOLA-2) including Laser Altimeter launched Nov. 7, 1996 by NASA and JPL.

Zuber et al The Mars Observer Laser Altimeter Investigation J. Geophys. Res. 97 p. 7781-7797.

Afzal Mars Observer Laser Altimeter: laser transmitter Applied Optics 33 p. 3184-3188.

Prizinsky Desktop Process Drives Technology House (Rapid Prototyping) Crain's Cleveland Business May 26, 1997, v. 18. n.21 p. 38.

Ashley Rapid Prototyping is Coming of Age Mechanical Engineering Jul. 1995 p. 63.

Waterman Rapid Prototyping DE Mar. 1997 p. 30.

Griffith et al Rapid Prototyping Technologies Rapid Prototyping 1998.

Ashley From CAD to Rapid Metal Tools Mechanical Engineering Jul. 1995 p. 75.

Bylinsky Industry's Amazing New Instant Prototypes Fortune Features Jan. 1998.

Hartwig Rapid 3D Modelers Design Engineer Mar. 1997 p. 38.

Marketed Machine: Helisys LOM 1015 Penn State University, PA 1998.

Marketed Machine: Stratsys FDM-2000 Penn State University, PA Jan. 1999.

* cited by examiner

METHOD FOR AUTOMATICALLY CREATING A DENTURE USING LASER ALTIMETRY TO CREATE A DIGITAL 3-D ORAL CAVITY MODEL AND USING A DIGITAL INTERNET CONNECTION TO A RAPID STEREOLITHOGRAPHIC MODELING MACHINE

CLAIM OF PRORITY DATE AND NOTICE OF CO-PENDING APPLICATIONS

The applicant claims a priority date of Nov. 15, 1999 the filing date on which a provisional patent application Ser. No. 60/165,474 for this formal application was filed and received by the United States Patent Office. There are no other co-pending related applications filed by the applicant as of the date of filing of this application.

BACKGROUND

1. Field of Invention

The invention concerns a method for rapidly and automatically making and supplying at least one denture on the basis of digital image information of a part or all of the human mouth, according to which this image information of the mouth is directly converted, after digital transmission via phone or internet, by means of the rapid prototyping technique and thus with a computer processing unit and a rapid prototyping machine, into a working usable disposal plastic denture for immediate use in the human mouth.

2. Prior Art

Dentures herein are defined as full or partial dentures. A partial denture is defined herein as one juxtaposed to a natural or implanted tooth. A full denture may consist of either a denture overfitting either the upper gums with all teeth removed or the lower gums with all teeth removed. Partial dentures as such are beyond the scope of this disclosure for technical, physical, economic, and other considerations inconsistent with an essential objection of the invention, namely, to make full dentures and replacements thereof inexpensive, rapidly obtainable, and disposably made of a plastic material comparable to the transition in the contact lens industry from permanent glass contacts to inexpensive disposable plastic contacts.

By rapid prototyping technique should be understood all techniques whereby an object is built layer by layer or point per point by adding or hardening material (also called free-form manufacturing). The best known techniques of this type are: stereo lithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; or fused deposition modeling, whereby a synthetic material is fused and is stacked according to a line pattern. A computer tomography scanner can provide the digital image information.

The model produced up to now according to the above-mentioned technique, can be a dental crown or other partial dental restoration such as an inlay that is an exact copy of the part as digitally stored in a computer, or it can be a prosthesis that fits perfectly to a matching part in the part of the body.

However, the dentures produced up to now, including three-dimensional images, do not take advantage of lower costs of delivering a finished upper and/or lower or full mouth denture directly to the consumer using rapid modeling or prototyping technology for mass production of these related but individualized dentures using robotics, computers, CAD programs, and modern plastics to substantially reduced the cost, eliminate the need for dentists, and deliver the finished denture in multiple disposable plastic sets to a consumer. Moreover, the dentures available and made today exhibit exterior styling and tooth structure that have no bearing or relationship to the user's teeth size and arrangement before their teeth were completely removed and the fact that digital storage technology and laser scanning now allows much wider latitude in denture style at lower cost and faster turnaround time.

Models for prostheses which are exact copies of real structures have been, for example, produced from medical images with the technique disclosed in the article "Integration of 3-D medical imaging and rapid prototyping to create stereo lithographic models" from T. M. BARKER et al., published in "Australasian Physical & Engineering Sciences in Medicine", vol. 16, no. 2, June 1993, pages 79–85.

Scanner data are transformed to a suitable format in a computer and the images are processed as a volume of voxels. The object is segmented prior to the meshing of the object surface and the creation of the stereo lithographic model. The obtained model cannot be used for registration, this is finding back a position on the patient.

As for the application of dental implants, attempts have already been made to use teeth of a provisional prosthesis as a reference. This provisional prosthesis is made on the basis of a mould. With a reconstruction by means of computer tomography scanner images on the basis of planes in which the bone is clearly visible, what is called a dental scan, one can see whether the position and the angle of the provisional teeth are correct in relation to the underlying bone, and one can make corrections. However, this is a time-consuming method and costly method employing tomography in a way different from the instant novel invention. Another prior art method consists in making a model of the jaw by means of the rapid prototyping technique and to make a template on the basis of this model, which is used during the surgery.

Heretofore, dental practice has been slow to address the need to quickly provide full dentures to the elderly and others needing it. The emphasis of the novel invention presented here is on the practicality of bringing a quick, relatively inexpensive product into the marketplace for delivery to people replacing original dentures or otherwise toothless with no obstructions.

Dentists are charging around $75.00 per tooth in preparation for a denture. For the denture itself, dentists are charging fees in the neighborhood of about $1400 or more. In major cities, according to some interviewed dental practitioners, it takes 2 weeks start to finish—$75 per tooth extraction, and an additional $1400 to $2400 for the dentures. Current full dentures centers all around the country offer so-called quickness at 2 weeks as opposed to maybe 6 to 8 weeks with an established dentist who of course does many other dental procedures.

In 1998 related U.S. Pat. No. 5,768,134 was issued to Swaelens et al. for a method for making a perfected medical model on the basis of digital image information of a part of the body. According to which this image information of a part of the body is converted, by means of what is called the rapid prototyping technique and thus with a processing unit and a rapid prototyping machine, into a basic model of which at least a part perfectly shows the positive or negative form of at least a portion of the part of the body. At least an artificial functional element with a useful function is added to the basic model as a function of the digital information and possibly as a function of additional external information.

In 1996 related U.S. Pat. No. 5,557,297 was issued to Hyde et al. for an aircraft based topographical data collection and processing system for rapidly and accurately determining the topography of land masses as well as individual x, y, z coordinates of discrete objects and/or terrain. This patent is hereby incorporated herein by reference.

In 1993 related U.S. Pat. No. 5,189,781 was issued to Weiss et al. for a rapid tool manufacturing method requiring first building an SFF pattern made of plastic. Rapid prototyping machinery currently available include a Helisys model LOM 1015, a 3D System's model SLA250 and Stratasys's model FDM-2000. These machines are complicated and do require regular service.

The term rapid prototyping (RP) refers to a class of technologies that can automatically construct physical models from Computer-Aided Design (CAD) data. These "three dimensional printers" allow designers to quickly create tangible prototypes of their designs, rather than just two-dimensional pictures. Such models have numerous uses.

In addition to prototypes, RP techniques can also be used to make tooling (referred to as rapid tooling) and even production-quality parts (rapid manufacturing). For small production runs and complicated objects, rapid prototyping is often the best manufacturing process available. Of course, "rapid" is a relative term. Most prototypes require from three to seventy-two hours to build, depending on the size and complexity of the object. This may seem slow, but it is much faster than the weeks or months required to make a prototype by traditional means such as machining. These dramatic time savings allow manufacturers to bring products to market faster and more cheaply. In 1994, Pratt & Whitney achieved "an order of magnitude cost reduction and time savings of 70 to 90 percent" by incorporating rapid prototyping into their investment casting process.

At least six different rapid prototyping techniques are commercially available, each with unique strengths. Because RP technologies are being increasingly used in non-prototyping applications, the techniques are often collectively referred to as solid free-form fabrication, computer automated manufacturing, or layered manufacturing. The latter term is particularly descriptive of the manufacturing process used by all commercial techniques. A software package "slices" the CAD model into a number of thin (e.g. 0.1 mm) layers, which are then built up one atop another. Rapid prototyping is an "additive" process, combining layers of paper, wax, or plastic to create a solid object.

In contrast, most machining processes (milling, drilling, grinding, etc.) are "subtractive" processes that remove material from a solid block. RP's additive nature allows it to create objects with complicated internal features that cannot be manufactured by other means. Of course, rapid prototyping is not perfect. Part volume is generally limited to 0.125 cubic meters or less, depending on the RP machine. Metal prototypes are difficult to make, though this should change in the near future. For metal parts, large production runs, or simple objects, conventional manufacturing techniques are usually more economical. These limitations aside, rapid prototyping is a remarkable technology that is revolutionizing the manufacturing process.

The Basic Process

Although several rapid prototyping techniques exist, all employ the same basic five-step process. The steps are:

Create a CAD model of the design
Convert the CAD model to STL format
Slice the STL file into thin cross-sectional layers
Construct the model one layer atop another
Clean and finish the model First, the object to be built is modeled using a Computer-Aided Design (CAD) software package. Solid modelers, such as Pro/ENGINEER, tend to represent 3-D objects more accurately than wire-frame modelers such as AutoCAD, and will therefore yield better results. The designer can use a pre-existing CAD file or may wish to create one expressly for prototyping purposes. The various CAD packages use a number of different algorithms to represent solid objects. To establish consistency, the STL (stereo lithography, the first RP technique) format has been adopted as the standard of the rapid prototyping industry. The second step, therefore, is to convert the CAD file into STL format. This format represents a three-dimensional surface as an assembly of planar triangles, "like the facets of a cut jewel." The file contains the coordinates of the vertices and the direction of the outward normal of each triangle. Because STL files use planar elements, they cannot represent curved surfaces exactly. Increasing the number of triangles improves the approximation, but at the cost of bigger file size. Large, complicated files require more time to pre-process and build, so until now with larger and more powerful computers, the designer had to balance accuracy with manageability to produce a useful STL file.

In the third step, a pre-processing program prepares the STL file to be built. Several programs are available, and most allow the user to adjust the size, location and orientation of the model. Build orientation is important for several reasons. First, properties of rapid prototypes vary from one coordinate direction to another. For example, prototypes are usually weaker and less accurate in the z (vertical) direction than in the x-y plane. In addition, part orientation partially determines the amount of time required to build the model. Placing the shortest dimension in the z direction reduces the number of layers, thereby shortening build time.

The preprocessing software slices the STL model into a number of layers from 0.01 mm to 0.7 mm thick, depending on the build technique. The program may also generate an auxiliary structure to support the model during the build. Supports are useful for delicate features such as overhangs, internal cavities, and thin-walled sections.

The fourth step is the actual construction of the part. Using one of several techniques (described in the next section) RP machines build one layer at a time from polymers, paper, or powdered metal. Most machines are fairly autonomous, needing little human intervention. The final step is post-processing. This involves removing the prototype from the machine and detaching any supports. Some photosensitive materials need to be fully cured before use. Prototypes may also require minor cleaning and surface treatment. Sanding, sealing, and/or painting the model will improve its appearance and durability.

Rapid Prototyping Techniques

Most commercially available rapid prototyping machines use one of six techniques. At present, trade restrictions severely limit the import/export of rapid prototyping machines and technology from the U.S.

Stereo Lithography

Patented in 1986, stereo lithography started the rapid prototyping revolution. The technique builds three-dimensional models from liquid photosensitive polymers that solidify when exposed to ultraviolet light. As shown in the figure below, the model is built upon a platform situated just below the surface in a vat of liquid epoxy or acrylate resin.

A low-power highly focused UV laser traces out the first layer, solidifying the model's cross section while leaving excess areas liquid.

Next, an elevator incrementally lowers the platform into the liquid polymer. A sweeper re-coats the solidified layer with liquid, and the laser traces the second layer atop the first. This process is repeated until the prototype is complete. Afterwards, the solid part is removed from the vat and rinsed clean of excess liquid. Supports are broken off and the model is then placed in an ultraviolet oven for complete curing.

Stereo lithography Apparatus (SLA) machines have been made since 1988 by 3D Systems of Valencia, Calif. To this day, 3D Systems is the industry leader, selling more RP machines than any other company. Because it was the first technique, stereo lithography is regarded as a benchmark by which other technologies are judged. Early stereo lithography prototypes were fairly brittle and prone to curing-induced warpage and distortion, but recent modifications have largely corrected these problems.

Laminated Object Manufacturing

In this technique, developed by Helisys of Torrance, Calif., layers of adhesive-coated sheet material are bonded together to form a prototype. The original material consists of paper laminated with heat-activated glue and rolled up on spools. As shown in the figure below, a feeder/collector mechanism advances the sheet over the build platform, where a base has been constructed from paper and double-sided foam tape. Next, a heated roller applies pressure to bond the paper to the base. A focused laser cuts the outline of the first layer into the paper and then cross-hatches the excess area (the negative space in the prototype). Cross-hatching breaks up the extra material, making it easier to remove during post-processing. During the build, the excess material provides excellent support for overhangs and thin-walled sections. After the first layer is cut, the platform lowers out of the way and fresh material is advanced. The platform rises to slightly below the previous height, the roller bonds the second layer to the first, and the laser cuts the second layer. This process is repeated as needed to build the part, which will have a wood-like texture.

In recent years Helisys has developed several new sheet materials, including plastic, water-repellent paper, and ceramic and metal powder tapes. The powder tapes produce a "green" part that must be sintered for maximum strength.

Selective Laser Sintering

Developed by Carl Deckard for his master's thesis at the University of Texas, selective laser sintering was patented in 1989. The technique uses a laser beam to selectively fuse powdered materials, such as nylon, elastomer, and metal, into a solid object. Parts are built upon a platform, which sits just below the surface in a bin of the heat-fusable powder. A laser traces the pattern of the first layer, sintering it together. The platform is lowered by the height of the next layer and powder is reapplied. This process continues until the part is complete. Excess powder in each layer helps to support the part during the build. DTM of Austin, Tex., produces SLS machines.

Fused Deposition Modeling

In this technique, filaments of heated thermoplastic are extruded from a tip that moves in the x-y plane. Like a baker decorating a cake, the controlled extrusion head deposits very thin beads of material onto the build platform to form the first layer. The platform is maintained at a lower temperature, so that the thermoplastic quickly hardens. After the platform lowers, the extrusion head deposits a second layer upon the first. Supports are built along the way, fastened to the part either with a second, weaker material or with a perforated junction. Stratasys, of Eden Prairie, Minn. makes a variety of FDM machines ranging from fast concept modelers to slower, high-precision machines. Materials include polyester, polypropylene, ABS, elastomers, and investment casting wax.

Solid Ground Curing

Developed by Cubital, solid ground curing (SGC) is somewhat similar to stereo lithography (SLA) in that both use ultraviolet light to selectively harden photosensitive polymers. Unlike SLA, SGC cures an entire layer at a time. Solid ground curing is also known as the solider process. First, photosensitive resin is sprayed on the build platform. Next, the machine develops a photo mask (like a stencil) of the layer to be built. This photo mask is printed on a glass plate above the build platform using an electrostatic process similar to that found in photocopiers. The mask is then exposed to UV light, which only passes through the transparent portions of the mask to selectively harden the shape of the current layer.

After the layer is cured, the machine vacuums up the excess liquid resin and sprays wax in its place to support the model during the build. The top surface is milled flat, and then the process repeats to build the next layer. When the part is complete, it must be de-waxed by immersing it in a solvent bath. Cubital America Inc. of Troy, Mich. distributes SGC machines in the U.S. The machines are quite big and can produce large models.

Ink-Jet Printing

Unlike the above techniques, Ink-Jet Printing refers to an entire class of machines that employ ink-jet technology. The first was 3D Printing (3DP), developed at MIT and licensed to Soligen Corporation, Extrude Hone, and others.

Parts are built upon a platform situated in a bin full of powder material. An ink-jet printing head selectively "prints" binder to fuse the powder together in the desired areas. Unbound powder remains to support the part. The platform is lowered, more powder added and leveled, and the process repeated. When finished, the green part is sintered and then removed from the unbound powder. Soligen uses 3DP to produce ceramic molds and cores for investment casting, while Extrude Hone hopes to make powder metal tools and products.

Sanders Prototype of Wilton, N.H. uses a different ink-jet technique in its Model Maker line of concept modelers. The machines use two ink-jets. One dispenses low-melt thermoplastic to make the model, while the other prints wax to form supports. After each layer, a cutting tool mills the top surface to uniform height. This yields extremely good accuracy, allowing the machines to be used in the jewelry industry.

3D Systems has also developed an ink-jet based system. The Multi-Jet Modeling technique uses an array of 96 separate print heads to rapidly produce thermoplastic models. If the part is narrow enough, the print head can deposit an entire layer in one pass. Otherwise, the head makes several passes.

Ballistic particle manufacturing was developed by BPM Inc., which has since gone out of business.

Applications of Rapid Prototyping

Rapid prototyping is widely used in the automotive, aerospace, medical, and consumer products industries. Although the possible applications are virtually limitless, nearly all fall into one of the following categories: prototyping, rapid tooling, or rapid manufacturing.

Prototyping

As its name suggests, the primary use of rapid prototyping is to quickly make prototypes for various purposes. Prototypes dramatically improve communication because most people find three-dimensional objects easier to understand than two-dimensional drawings. Such improved understanding leads to substantial cost and time savings. As Pratt & Whitney executive Robert P. DeLisle noted: "We've seen an estimate on a complex product drop by $100,000 because people who had to figure out the nature of the object from 50 blueprints could now see it." Effective communication is especially important in this era of concurrent engineering. By exchanging prototypes early in the design stage, manufacturing can start tooling up for production while the art division starts planning the packaging, all before the design is finalized.

Prototypes are also useful for testing a design, to see if it performs as desired or needs improvement. Engineers have always tested prototypes, but RP expands their capabilities. First, it is now easy to perform iterative testing: build a prototype, test it, redesign, build and test, etc. Such an approach would be far too time-consuming using traditional prototyping techniques, but it is easy using RP. In addition to being fast, RP models can do a few things metal prototypes cannot. For example, Porsche used a transparent stereo lithography model of the 911 GTI transmission housing to visually study oil flow. Snecma, a French turbo machinery producer, performed photo elastic stress analysis on a SLA model of a fan wheel to determine stresses in the blades.

Rapid Tooling

A much-anticipated application of rapid prototyping is rapid tooling, the automatic fabrication of production quality machine tools. Tooling is one of the slowest and most expensive steps in the manufacturing process, because of the extremely high quality required. Tools often have complex geometries, yet must be dimensionally accurate to within a hundredth of a millimeter. In addition, tools must be hard, wear-resistant, and have very low surface roughness (about 0.5 micrometers root mean square). To meet these requirements, molds and dies are traditionally made by CNC-machining, electro-discharge machining, or by hand. All are expensive and time consuming, so manufacturers would like to incorporate rapid prototyping techniques to speed the process. Peter Hilton, president of Technology Strategy Consulting in Concord, Mass., believes that "tooling costs and development times can be reduced by 75 percent or more" by using rapid tooling and related technologies.

Rapid tooling can be divided into two categories, indirect and direct.

Indirect Tooling

Most rapid tooling today is indirect: RP parts are used as patterns for making molds and dies. RP models can be indirectly used in a number of manufacturing processes:

Vacuum Casting: In the simplest and oldest rapid tooling technique, an RP positive pattern is suspended in a vat of liquid silicone or room temperature vulcanizing (RTV) rubber. When the rubber hardens, it is cut into two halves and the RP pattern is removed. The resulting rubber mold can be used to cast up to 20 polyurethane replicas of the original RP pattern.

A more useful variant, known as the Keltool powder metal sintering process, uses the rubber molds to produce metal tools. Developed by 3M and now owned by 3D Systems, the Keltool process involves filling the rubber molds with powdered tool steel and epoxy binder. When the binder cures, the "green" metal tool is removed from the rubber mold and then sintered. At this stage the metal is only 70% dense, so it is infiltrated with copper to bring it close to its theoretical maximum density. The tools have fairly good accuracy, but their size is limited to under 25 centimeters.

Sand Casting: An RP model is used as the positive pattern around which the sand mold is built. LOM models, which resemble the wooden models traditionally used for this purpose, are often used. If sealed and finished, an LOM pattern can produce about 100 sand molds.

Investment Casting: Some RP prototypes can be used as investment casting patterns. The pattern must not expand when heated, or it will crack the ceramic shell during autoclaving. Both Stratasys and Cubital make investment casting wax for their machines. Paper LOM prototypes may also be used, as they are dimensionally stable with temperature. The paper shells burn out, leaving some ash to be removed.

To counter thermal expansion in stereo lithography parts, 3D Systems introduced QuickCast, a build style featuring a solid outer skin and mostly hollow inner structure. The part collapses inward when heated. Likewise, DTM sells Trueform polymer, a porous substance that expands little with temperature rise, for use in its SLS machines.

Injection molding: CEMCOM Research Associates, Inc. has developed the NCC Tooling System to make metal/ceramic composite molds for the injection molding of plastics. First, a stereo lithography machine is used to make a match-plate positive pattern of the desired molding. To form the mold, the SLA pattern is plated with nickel, which is then reinforced with a stiff ceramic material. The two mold halves are separated to remove the pattern, leaving a matched die set that can produce tens of thousands of injection moldings.

Direct Tooling

To directly make hard tooling from CAD data is the objective of rapid tooling. RapidTool: A DTM process that selectively sinters polymer-coated steel pellets together to produce a metal mold. The mold is then placed in a furnace where the polymer binder is burned off and the part is infiltrated with copper (as in the Keltool process). The resulting mold can produce up to 50,000 injection moldings. In 1996 Rubbermaid produced 30,000 plastic desk organizers from an SLS-built mold. This was the first widely sold consumer product to be produced from direct rapid tooling.

Extrude Hone, in Irwin Pa., will soon sell a machine, based on MIT's 3D Printing process, that produces bronze-infiltrated PM tools and products.

Laser-Engineered Net Shaping (LENS) is a process being developed at Sandia National Laboratories and Stanford University that will create metal tools from CAD data. Materials include 316 stainless steel, Inconel 625, H13 tool steel, tungsten, and titanium carbide cermets. A laser beam melts the top layer of the part in areas where material is to be added. Powder metal is injected into the molten pool, which then solidifies. Layer after layer is added until the part is complete. Unlike traditional powder metal processing, LENS produces fully dense parts, since the metal is melted, not merely sintered. The resulting parts have exceptional mechanical properties.

Direct AIM (ACES Injection Molding): A technique from 3D Systems in which cores are used with traditional metal molds for injection molding of high and low density polyethylene, polystyrene, polypropylene and ABS plastic. Very good accuracy is achieved for fewer than 200 moldings. Long cycle times (e.g. five minutes) are required to allow the molding to cool enough that it will not stick to the SLA core.

In another variation, cores are made from thin SLA shells filled with epoxy and aluminum shot. Aluminum's high conductivity helps the molding cool faster, thus shortening cycle time. The outer surface can also be plated with metal to improve wear resistance. Production runs of 1000–5000 moldings are envisioned to make the process economically viable.

LOM Composite: Helysis and the University of Dayton are working to develop ceramic composite materials for Laminated Object Manufacturing. LOM Composite parts would be very strong and durable, and could be used as tooling in a variety of manufacturing processes.

Sand Molding: At least two RP techniques can construct sand molds directly from CAD data. DTM sells sand-like material that can be sintered into molds, while Soligen 3D Printing machines can produce ceramic molds as well.

Rapid Manufacturing

A natural extension of RP is rapid manufacturing (RM), the automated production of salable products directly from CAD data. Currently only a few final products are produced by RP machines.

For short production runs RM is very cheap, since it does not require tooling. RM is also ideal for producing custom parts tailored to the user's exact specifications. A University of Delaware research project uses a digitized 3-D model of a person's head to construct a custom-fitted helmet. NASA is experimenting with using RP machines to produce space-suit gloves fitted to each astronaut's hands.

The other major use of RM is for products that simply cannot be made by subtractive (machining, grinding) or compressive (forging, etc.) processes. This includes objects with complex features, internal voids, and layered structures. Specific Surface of Franklin, Mass. uses RP to manufacture complicated ceramic filters that have eight times the interior surface area of older types. The filters remove particles from the gas emissions of coal-fired power plants.

Therics, Inc. of NYC is using RP's layered build style to develop "pills that release measured drug doses at specified times during the day" and other medical products.

As with the novel invention described below rapid prototyping is starting to change the way companies design and build products. One such improvement is increased speed. "Rapid" prototyping machines are beyond the state of the art by all current standards. By using faster computers, more complex control systems, and improved materials, RP manufacturers are on the verge of dramatically reducing build time. For example, Stratasys recently (January 1998) introduced its FDM Quantum machine, which can produce ABS plastic models 2.5–5 times faster than previous FDM machines.

Today's commercially available machines are accurate to 0.08 millimeters in the x-y plane, but less in the z (vertical) direction. Improvements in laser optics and motor control should increase accuracy in all three directions.

The rapid prototyping industry will continue to grow, both worldwide and at home. The United States currently dominates the field, but Germany, Japan, and Israel are making inroads. In time RP will spread to less technologically developed countries as well. With more people and countries in the field, RP's growth will accelerate further.

One future application is Distance Manufacturing on Demand, a combination of RP and the Internet that will allow designers to remotely submit designs for immediate manufacture. Researchers at UC-Berkeley, among others, are developing such a system.

SUMMARY OF THE INVENTION

The invention aims to remedy these disadvantages and to provide a method for making a working usable disposal plastic full upper and/or lower denture for immediate use in the human mouth on the basis of digital image information of the oral cavity whereby the image information optimally used in conjunction to previously prepared or "canned" cosmetic or styled digital models of the outer appearance of the dentures. The novel method contemplates a service and process wherein the actual teeth of a person are scanned and digitized early in life for use later in life when full upper and other lower dentures are needed and manufactured in accordance with the disclosed novel method.

This aim is reached according to the invention when at least a full upper or lower plastic disposable artificial denture is made using digital data of an image of the oral cavity without teeth is created and merged with data depicting a specific outer surface or style and a denture is created and sent directly to the consumer without employing the skills of a dentist during the step of creating an image of the cavity into which the denture is to fit.

By subsequently converting the image of the toothless oral cavity with the additional information for the control of a rapid prototyping machine, there is a digital link of the oral cavity data to reality and a perfected model is obtained which does not only have the requisite shape at the juxtaposed surfaces of the disposable denture and the oral cavity of a certain part of the body, but which also contains either an actual archived model of the person's oral cavity prior to complete tooth removal or artificial elements which are added based on personal preference as a function of image information. Therefore, an actual plastic low cost disposable denture can be made according to the method, which fits perfectly to existing gums and which in the case of a stored archival image has a feel once familiar and comforting to the user and which forms a unique heretofore unrealized functional element of any artificial denture.

Thus, it is a primary object of the invention to provide a method for making an actual plastic low cost disposable denture which fits perfectly to existing gums using a stored archival image so that the denture to the user has a familiar feel comforting to the user based on an actual prior teeth arrangement and actual size of various teeth which forms a unique heretofore unrealized functional element of any artificial denture, namely, replication of the actual mastication surfaces once disposed in the user's mouth. Another object of the invention is to provide a processing for rapidly making a complete upper and/or lower disposable plastic denture using a laser scanner, CAD computer program for converting a scanned image into a digital file, and a pre-stored digital image of the outer non-juxtaposing surface of the denture, and then constructing a model and actual denture using currently known and used rapid modeling techniques at a remote rapid modeling facility adapted to receive the digital images and use them to rapidly make a denture.

Still another object of my invention is to provide a selective procedure wherein a person desiring a full mouth upper or lower denture to match a still existing opposite dental structure can use a pre-stored model of his previously existing oral cavity and teeth as the model for the outer surface of the artificial denture.

Still yet another object of my invention is to provide a procedure wherein a person desiring a full mouth upper and lower denture to match his or her pre-existing dental structure can use a pre-stored model of his previously existing oral cavity and teeth as the model for the outer surfaces of the artificial upper and lower dentures.

One other object is to give the entire full denture market rapid access to a method for rapidly obtaining replacement and original dentures in a variety of styles, including simulated gold teeth, without having to wait for an appointment with a dentist and at a cost such that multiple styles may be acquired at a fraction of the cost one present day full denture.

A more general object of my invention is to provide a prospective patient the option of foregoing the expense of the services of a dentist for replacement upper and/or full mouth dentures.

Yet another object of the invention is to address a need in the full denture market for individual expression such as have been previously exhibited by custom and individualized inlays and caps incorporating precious stones and precious metals.

BRIEF DESCRIPTION OF THE DRAWING

Various objects, features and alternate advantages of the invention will be more fully appreciated as the same becomes better understood with reference to the following detailed description of the present invention when considered in connection with the accompanying drawing. Thus, in order to better explain the characteristics of the novel combination of steps of the invention, the following preferred embodiment of a method for making and directly delivering a custom fitted plastic disposable artificial full upper and/or lower denture on the basis of digital image information of the oral cavity is fully disclosed as an example only without being limitative in any way in which.

DETAILED DESCRIPTION OF A PREFERRED METHOD

Figure 1:
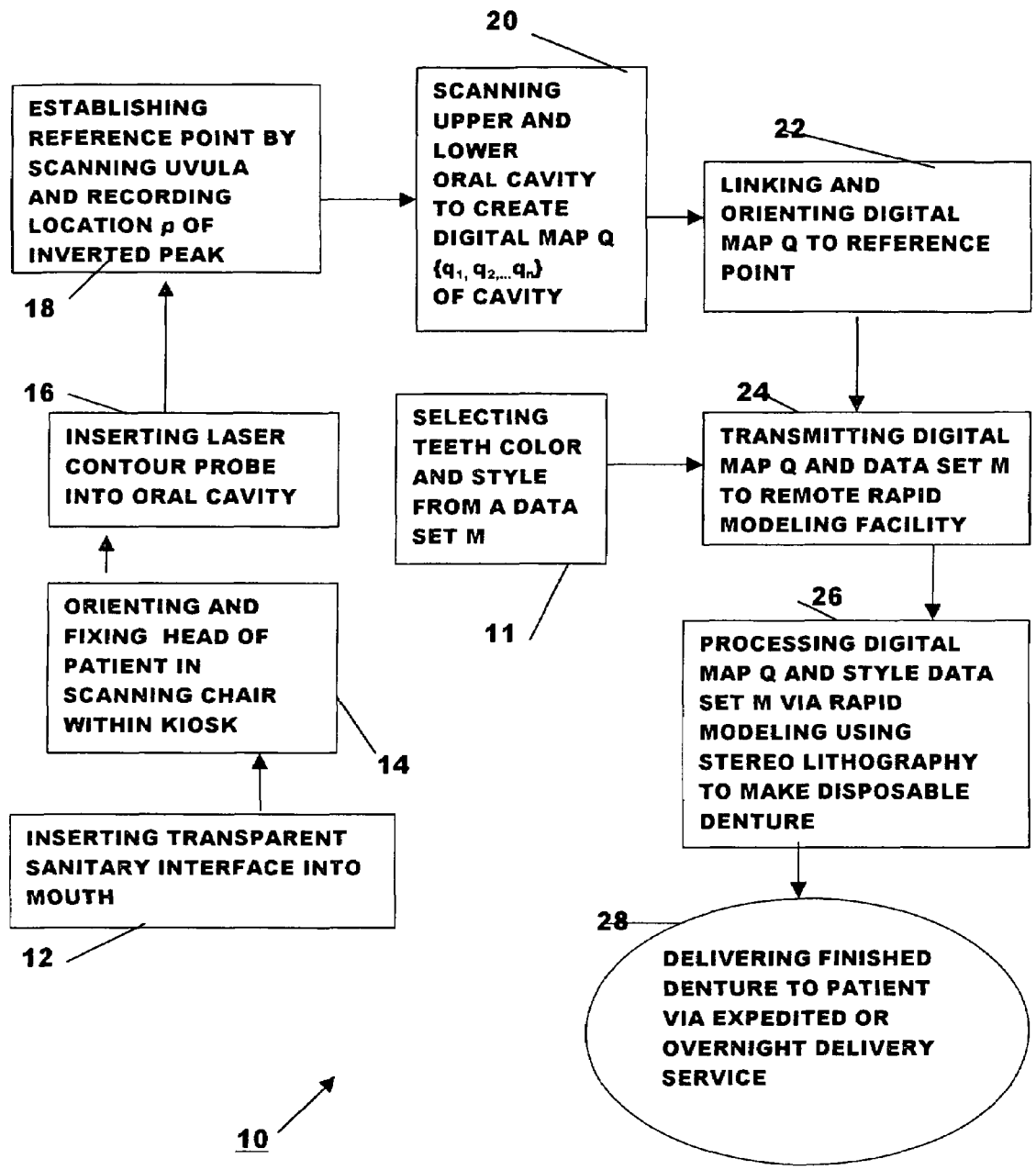
FIG. 1 shows a block diagram of a method for making a denture according to the invention; and, FIG. 2 is a diagram showing the process using a laser scanner connected to a laser scanner computer controller interconnected to another facility controlling computer at a rapid prototyping facility.

Referring in detail to FIG. 1, there is shown a preferred embodiment of a novel method 10 according to the invention disclosed herein and as adapted for use as a means for creating low cost disposable plastic dentures.

The method of making a denture from digital information corresponding to at least a part of a human oral cavity wherein the digital information is used to generate information for rapid prototyping of the denture is substantially and newly improved by the steps of adding to the digital information, additional digital data selected from an archive of digital data selected from a group of digital data consisting of artificial image digital data and actual image digital data, which additional digital data depicts a denture, the denture being selected from the group consisting of a full upper denture and a full lower denture, the digital information and the additional digital data being based on image information in a form wherein all of the digital information and the additional data are combined and viewable as a computer generated composite image; and the further step of carrying out the rapid manufacturing of a full denture using said digital information with the said additional digital data whereby the denture made substantially resembles the digital data viewable as the computer generated composite image. The new method further has a step of including using a computer system as a part of the adding to the digital information step. And the new method also having a processing step where the artificial image data is used in producing the denture with the aid of a computer system.

The novel method 10 includes using a laser scanning system such as that disclosed in U.S. Pat. No. 5,940,170 issued to Berg et al. on Aug. 17, 1999 to automatically position and move another more accurate laser scanner wand inside the mouth of a person. The Berg et al. patent disclosure is hereby incorporated herein by reference pursuant to MPEP 608.01(p) A. The resolution afforded by Berg et al. is adequate to locate the mouth and determine a reference point based on imaging the uvula or an intersection of a line with the mid-line of the tongue. Berg et al. provides a spatial resolution of approximately 0.050 inches in x, y (length, height) and 0.2 inches in z (range to the pixel) which is adequate for robotically positioning a person's head in a restraint attached to a chair and determining a reference point for orienting a high resolution laser scanning wand such as disclosed in U.S. Pat. No. 4,935,635 which issued on Jun. 19, 1990 to O'Harra and which is incorporated herein by reference thereto.

The O'Harra laser scanning wand and associated system provides a resolution of 50 microns and has a diameter of approximately 16 mm. The O'Harra wand proves ideal for a denture kiosk for using the method of the novel invention. It's ease of use including rapid setup, rapid data acquisition, and improved data processing using Y2K computer processors makes this structure most suitable to implement the novel method disclosed herein.

Referring again to FIG. 1, there is shown a flow diagram of the method 10 wherein an inserting step 12 specifically requires inserting a transparent sanitary interface into the mouth of a person. This is a minimum sanitary requirement to implement the method 10 in a kiosk structure. By kiosk structure is meant a free standing room size enclosure manned by a dental assistant or other personnel. The kiosk contains a computer controlled dental chair adapted by a computer to receive a person, comfortably restrain and fix the head of the body in a position with padded bolsters controlled by computer to effect restraint of the head in a preferred position. Once the head is fixed, a computer generated voice or assistant instructs the person to open his or her mouth. An O'Harra wand is introduced into the mouth. The wand is covered with a laser transparent sanitary cover, namely, a completely transparent Saran™ plastic wrap or like material in the shape of a condom, for example. Thus, a preferred next step in the method is an inserting step 12 comprising inserting a transparent sanitary interface into the person or patient's mouth.

A next preferred step in the method is an orienting step 14 comprising orienting and fixing the head of the person or patient in a chair. The chair is a scanning chair located within a kiosk used in conjunction with an O'Harra wand and the robotic laser device of Berg et al. adapted for automatically orienting the head of the person and scanning the open mouth cavity to fix a point relative to the uvula or relative to the tongue after either is scanned. In an alternative embodiment, the O'Harra wand is used both for determining a reference point from a topographic scan of the uvula or the tongue and for scanning the gums and mouth to determine and create a digital topographic map of the gums for the interior aspects of the upper and/or lower dentures. Thus, the laser contouring step is included in the inserting step 16 comprising inserting a laser contour probe, the O'Harra wand for example, in the oral cavity or mouth of the patient. The referencing step 18 comprises establishing a reference point by scanning the uvula to determine the coordinates of its inverted point, a unique anatomical entity common to virtually all persons which forms a natural physical point within the mouth, and recording the x, y, and z coordinates or location p of the inverted peak of the uvula. Alternatively, or conjunctively for improved accuracy of fitting the dentures, the tongue, as relaxed on the floor of the mouth, is scanned and a straight medial line extending from the tip of the tongue towards the rear of the tongue is calculated, digitally stored, and intersected at 20 and/or 40 millimeters, for example, from the tip of the tongue to establish an intersection and a location p' along with associated coordinates x', y', and z' and optionally a location p" along with associated coordinates x", y", and z".

The scanning step 20 involves laser scanning, using the O'Harra wand or the Berg scanner, of the upper and lower oral cavity to create a digital map Q comprised of the set of coordinates $\{q_1, q_2, q_3, \ldots q_n\}$ which represent the entire oral cavity referenced to the point p, and/or the point p', and/or the point p". The linking step 22 is performed by a computer program wherein CAD processing results in linking and orienting the digital map Q to one or more predetermined reference points p, and/or the point p', and/or the point p" and so on.

The kiosk as constructed according to the method of the invention is connected to a rapid modeling facility remotely located away from the kiosk. The computer at the kiosk is connected via the internet, wireless satellite link, wire digital phone service, a combination thereof, or comparable means for multiple input and transmission of data into the facility which data represents a model for making a specific set of dentures including digital data representing a style M representing a configuration or style for the outer surface appearance of the artificial teeth and artificial gums whereas the contours and shapes of the actual gums used to support the dentures are digitally represented by the digital topographic map Q.

Preferably, the map Q and the map for the style M are merged at the kiosk in a process for creating computer display image of the proposed finished artificial dentures which can be automatically rotated in various planes to provide a variety of views to patient, person, and buyer. In the process, the merged and displayed image N is combined with a digital scanned image of the face of the patient to provide the patient with a view R which includes the artificial dentures inside the person's mouth. The view R is digitally manipulated to show various views with the person's lips in different positions, e.g. smiling and frowning with the mouth partially open, to allow the person to obtain a feel how the product will look when inserted and worn.

After examining the various views R, $R_1$, $R_2$, ... $R_n$, the person engages in a process wherein various purchase options are exercised and an order for disposable plastic artificial dentures is processed. The order, for example, may consist of a request for multiple styles M with the same underlying contours corresponding to the digital map Q. Alternatively, the order may consist of an order for merely an upper or a lower denture.

Figure 2:
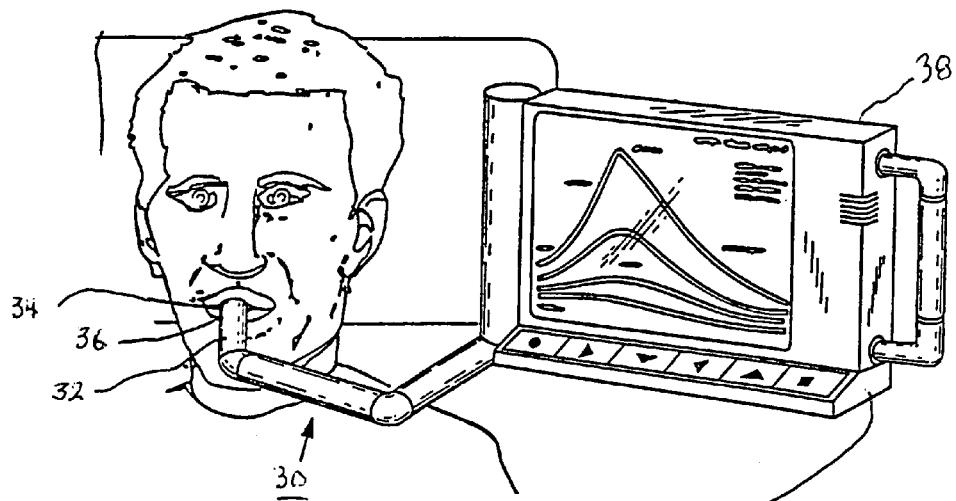
Figure 2:
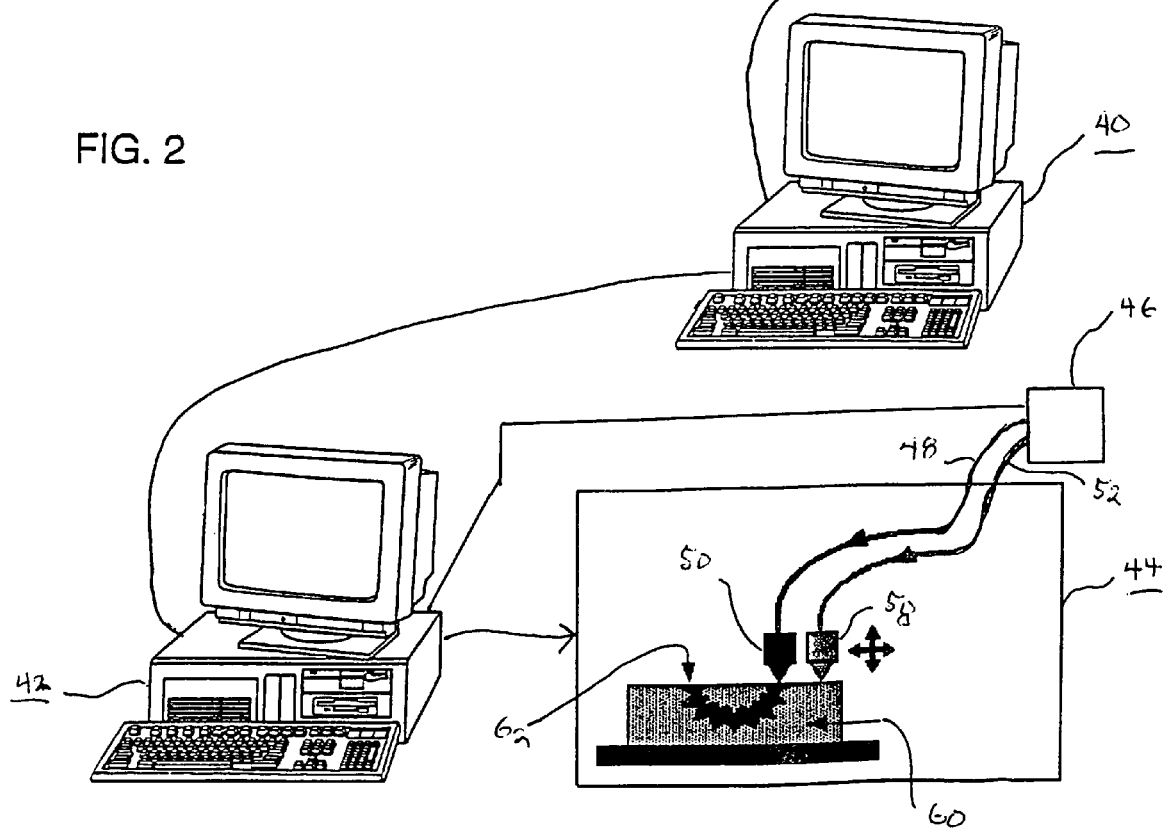

Referring to FIG. 2, there is shown an O'Harra laser scanner 30 or mapping device for obtaining a digital topographic map of the oral cavity. The scanner 30 has an outer housing 32 and a probe 34, which extends into the mouth. At one side of the probe 34 at the end thereof, capable of orientation in any direction, is a beam scan window 36 through which a collimated or focused laser beam is projected and scanned to obtain topographic information and data by triangulation.

A controller and operations monitor for the probe 34 is connected to a computer 40 where the topological data is processed, stored, displayed as an image on the compute screen. The computer 40 also calculates the reference point p and related reference points. Information and data is transferred via Internet or wireless transmission, for example, to a second computer 42 that controls a rapid prototyping facility 44. The computer 42 is connected to an interface 46 which outputs to a model fiber 48 and a support fiber 52 connected to a heated model 3D scanner head 50 and a heated support 3D scanner head 58, respectively. The scanner head 58 scans support material 60 whereas the model scanner head 50 creates a solid object 62 made of ABS plastic, for example, using in this cased fused deposition modeling technology with which it is relatively easy to change colors.

Partial dentures which require fitting to another tooth are not within the scope of the invention because dentures which are designed to fit within a space between teeth not supported on each side are well-known to require multiple adjustments to fit properly as the support teeth on each side shift significantly after a partial denture is installed and to a lesser extent before the denture is installed but dependent upon the length of time between the mapping of the space for the partial denture and the installation thereof. Thus, the viability and commercialization of the novel for partial dentures has not been tested. Partial dentures made by this process would still require the professional services of a dentist because of the interaction and interfitting necessary with adjoining teeth and would thereby be so much more expensive as to disable the disposability and multiplicity features of the dentures created by the novel process. Some partial dentures require metal fittings for interconnection that must be adjusted by hand to avoid injury to gum tissue supporting remaining teeth. The rapid model procedure within the novel process is not yet suitable for making metal tabs and the like connected to the plastic denture when required.

As shown in FIG. 1, the transmitting step 24 of transmitting a digital map Q and a data set M to a remote rapid modeling facility or RMF such as that described in U.S. Pat. No. 5,189,781 issued on Mar. 2, 1993 to Weiss et al., which patent is hereby incorporated herein by reference. Using the Weiss facility multiple sets of disposable plastic dentures are manufactured and the molds retained for making future reorders. Alternatively, the rapid model methods disclosed and taught by Schmitt et al. in U.S. Pat. No. 5,823,778 issued on Oct. 20, 1998 are utilized to machine the interior map Q for a denture set from a machinable plastic with the exterior style M having been preselected and premodeled and molded at the RMF. In the processing step 26 processing of the digital map Q and style data set M via rapid modeling at an RMF occurs using stereo lithography, for example, to make a mold or model from which ultimately a disposable plastic realistic artificial denture is made.

Using today's various overnight delivery services, such as now available by the United States Postal service as express mail, from Federal Express Corporation, and from United Parcel Service Corporation, for example, delivering step 28 is realized. Accordingly, delivering the finished denture to the person or patient via an expedited or overnight delivery service provider completes an essential step in the novel process.

It is to be understood that the above-identified preferred current method of the invention is merely illustrative of the preferred embodiment of the invention at the present time. Numerous and varied other arrangements of the essential steps of the invention as set forth in the claims can readily be devised using this description as a template in accordance with the principles of the present invention without departing from its spirit and scope as encompassed by the doctrine of equivalents.

What is claimed is:

1. A method of making a disposable dentures made of plastic usable in rapid model prototype manufacturing from digital information corresponding to a part of a human oral cavity wherein the digital information is used to generate information for rapid prototyping of the denture, the method further comprising:
   (a) adding to the digital information, additional digital data selected from archive of digital data, which additional data depicts both an upper and a lower denture and which digital information and said additional digital information is based on image information in a form wherein all of said digital data are viewable as a computer generated composite image;
   (b) rapid model prototype manufacturing of said dentures using said digital information with the added data to make a matching set of upper and lower dentures wherein the matching set of upper and lower dentures made substantially resembles the digital data viewable as the computer generated composite image; and
   (c) further including as part of said step of adding to the digital information, the step of processing at least said artificial image data used in producing said dentures using a CAD programmed computer system wherein a style comprising of shape, color, size, and texture is selected.

2. A method of making disposable dentures made of plastic usable in rapid model prototype manufacturing from digital information corresponding to a part of a human oral cavity wherein the digital information is used to generate information for rapid prototyping of the denture, the method further comprising:
   adding additional digital data to the digital information, said additional digital data being selected from an archive of digital data, which additional data depicts an upper and a lower denture, said additional digital data being derived from image information acquired by a laser topological image scan of the human oral cavity without teeth therein;
   rapid model prototype manufacturing of said dentures using said digital information with the added digital data to make a matching set of upper and lower disposable plastic dentures wherein the non-juxtaposing surfaces of said matching set of upper and lower dentures substantially resembles digital data stored from a laser topological scan image of the human oral cavity for teeth previously therein.

3. In a method of making a denture from digital information corresponding to an image of at least a part of a human oral cavity, said human oral cavity previously containing a plurality of natural teeth at a prior point in time, wherein the digital information is used to generate digital information for manufacturing of the denture, the improvement comprising:
   (a) said manufacturing comprising an initial step of scanning and storing a first digital image of said human oral cavity at a first point in time when the oral cavity contains a plurality of natural teeth, said scanning at a first scanning site; and subsequently at another point forward in time;
   (b) said manufacturing further comprising a step of scanning and storing a second digital image of said human oral cavity when the oral cavity no longer contains one or more of said natural teeth at a second scanning site, and subsequently at another point in time and at a remote manufacturing site digitally connected to said second site, said manufacturing further comprising the step of rapid prototype manufacturing of a denture at the remote manufacturing site;
   (c) at said prior point in time, preparing and digitally storing a selectable digital image of at least one surface of an actual tooth from a scan of the actual tooth inside the human oral cavity to create a group of actual image digital data;
   (d) adding to the digital information, additional digital data selected from an archive of digital data selected from a group of digital data consisting of artificial image digital data and actual image digital data, which additional digital data depicts a denture,
   (e) last said denture being selected from the group consisting of a full upper denture and a full lower denture, said digital information and said additional digital data being based on image information in a form wherein all of said digital information and said additional data are combined and viewable as a computer generated composite image;
   (f) using a plastic material for rapid model prototype manufacturing of at least one full denture using said digital information with the said additional digital data whereby the denture made substantially resembles the digital data viewable as the computer generated composite image; including using a computer system as a part of said adding to the digital information;
   (g) constructing an actual denture using all of said digital information and said additional data combined at a remote rapid modeling facility adapted to receive and use said digital images to rapidly make a disposable denture;
   (h) using an overnight delivery service system to deliver said constructed denture from said remote rapid modeling facility to a point of distribution accessible to the denture user; and,
   (i) including processing at least said artificial image data used in producing said denture using a computer system.

4. The method according to claim 1, wherein said additional digital data comprises a reference point derived from archived actual image digital data, and said archived actual image data being derived at least in part from a laser scan of the oral cavity having a pre-existing set of teeth located substantially in a plane and wherein in the rapid manufacturing process a plastic material is used to create the denture and for making the denture disposable.

5. The method according to claim 4, wherein the pre-existing set of teeth is a pre-existing artificial denture.

6. The method according to claim 4, wherein the pre-existing set of teeth comprises natural teeth and partially restored teeth.

7. The method according to claim 4, wherein the pre-existing set of teeth consists of natural teeth.

* * * * *